(12) United States Patent
Shea et al.

(10) Patent No.: US 11,344,432 B2
(45) Date of Patent: May 31, 2022

(54) ORTHOPEDIC IMPLANT AUGMENTS

(71) Applicant: Smith & Nephew, Inc., Memphis, TN (US)

(72) Inventors: Jeffrey J. Shea, Memphis, TN (US); Nathaniel M. Quinn, Arlington, TN (US); Daniel R. Goldberg, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 413 days.

(21) Appl. No.: 16/460,817

(22) Filed: Jul. 2, 2019

(65) Prior Publication Data
US 2019/0321195 A1     Oct. 24, 2019

Related U.S. Application Data

(63) Continuation of application No. 15/653,055, filed on Jul. 18, 2017, now Pat. No. 10,383,744, which is a
(Continued)

(51) Int. Cl.
*A61F 2/46* (2006.01)
*A61B 17/68* (2006.01)
(Continued)

(52) U.S. Cl.
CPC ............... *A61F 2/46* (2013.01); *A61B 17/68* (2013.01); *A61B 17/8061* (2013.01);
(Continued)

(58) Field of Classification Search
CPC ...... A61F 2/4609; A61F 2/46; A61F 2/30734; A61F 2002/30736; A61B 17/68; A61B 17/8061
See application file for complete search history.

(56) References Cited

U.S. PATENT DOCUMENTS 3,874,003 A    4/1975  Moser et al.
3,882,550 A    5/1975  Karpf et al.
(Continued)

FOREIGN PATENT DOCUMENTS

CN    2159767 Y    3/1994
CN    2217965 Y    1/1996
(Continued)

OTHER PUBLICATIONS

Chinese Office Action for CN Patent Application No. 201811129114.0, dated Dec. 1, 2020, 24 pages.
(Continued)

*Primary Examiner* — Ellen C Hammond
(74) *Attorney, Agent, or Firm* — KDB (57) ABSTRACT

Systems, methods and devices for providing orthopedic implant augments are provided which have fastener locking mechanisms. The augments include a surface for mating with an implant component and a surface for interfacing with a patient's bone. The fastener locking mechanisms are aligned such that the augment may be locked in a variety of orientations while maintaining close contact with both an implant and a patient's bone. The alignment of the locking mechanisms provides variability and adjustability to the augment to address a variety of bone anatomies and requirements.

11 Claims, 4 Drawing Sheets

Related U.S. Application Data continuation of application No. 14/363,775, filed as application No. PCT/US2012/068219 on Dec. 6, 2012, now Pat. No. 9,707,097.

(60) Provisional application No. 61/567,971, filed on Dec. 7, 2011.

(51) Int. Cl.
  *A61B 17/80* (2006.01)
  *A61F 2/30* (2006.01)
  *A61F 2/34* (2006.01)
  *A61B 17/86* (2006.01)

(52) U.S. Cl.
  CPC ...... *A61F 2/30734* (2013.01); *A61B 17/8052* (2013.01); *A61B 17/86* (2013.01); *A61F 2/34* (2013.01); *A61F 2002/30131* (2013.01); *A61F 2002/30433* (2013.01); *A61F 2002/30736* (2013.01)

(56) References Cited

U.S. PATENT DOCUMENTS

| | | | |
|---|---|---|---|
| 3,894,297 A | 7/1975 | Mittelmeier et al. | |
| 4,141,088 A | 2/1979 | Treace et al. | |
| 4,437,193 A | 3/1984 | Oh | |
| 4,473,068 A | 9/1984 | Oh | |
| 4,475,549 A | 10/1984 | Oh | |
| 4,566,138 A | 1/1986 | Lewis et al. | |
| 4,612,160 A | 9/1986 | Donlevy et al. | |
| 4,623,352 A | 11/1986 | Oh | |
| 4,632,111 A | 12/1986 | Roche | |
| 4,666,450 A | 5/1987 | Kenna | |
| 4,673,409 A | 6/1987 | Van Kampen | |
| 4,676,799 A | 6/1987 | Legrand | |
| 4,704,127 A | 11/1987 | Averill et al. | |
| 4,718,908 A | 1/1988 | Wigginton et al. | |
| 4,795,469 A | 1/1989 | Oh | |
| 4,883,490 A | 11/1989 | Oh | |
| 4,888,024 A | 12/1989 | Powlan | |
| 4,904,265 A | 2/1990 | MacCollum et al. | |
| 4,955,919 A | 9/1990 | Pappas et al. | |
| 4,959,072 A | 9/1990 | Morscher et al. | |
| 4,990,149 A | 2/1991 | Fallin | |
| 4,995,883 A | 2/1991 | Demane et al. | |
| 4,997,447 A | 3/1991 | Shelley | |
| 5,047,033 A | 9/1991 | Fallin | |
| 5,078,746 A | 1/1992 | Gamer | |
| 5,080,677 A | 1/1992 | Shelley | |
| 5,108,452 A | 4/1992 | Fallin | |
| 5,133,764 A | 7/1992 | Pappas et al. | |
| 5,176,711 A * | 1/1993 | Grimes | A61F 2/4684 623/22.22 |
| 5,192,329 A | 3/1993 | Christie et al. | |
| 5,193,679 A | 3/1993 | White | |
| 5,211,665 A | 5/1993 | Ku | |
| 5,217,499 A | 6/1993 | Shelley | |
| 5,226,917 A | 7/1993 | Schryver | |
| 5,310,408 A | 5/1994 | Schryver et al. | |
| 5,314,487 A | 5/1994 | Schryver et al. | |
| 5,324,291 A | 6/1994 | Ries et al. | |
| 5,326,367 A | 7/1994 | Robioneck | |
| 5,326,368 A | 7/1994 | Collazo | |
| 5,350,381 A | 9/1994 | Melton | |
| 5,358,532 A | 10/1994 | Evans et al. | |
| 5,370,703 A | 12/1994 | Willert et al. | |
| 5,387,241 A | 2/1995 | Hayes | |
| 5,405,005 A | 4/1995 | White | |
| 5,405,392 A | 4/1995 | Deckner | |
| 5,456,717 A | 10/1995 | Zweymuller et al. | |
| 5,507,825 A | 4/1996 | Frei | |
| 5,507,830 A | 4/1996 | DeMane et al. | |
| 5,549,702 A | 8/1996 | Ries et al. | |
| 5,571,105 A | 11/1996 | Gundolf | |
| 5,593,446 A | 1/1997 | Kuoni | |
| 5,641,323 A | 6/1997 | Caldarise | |
| 5,676,704 A | 10/1997 | Ries et al. | |
| 5,755,720 A | 5/1998 | Mikhail | |
| 5,755,793 A | 5/1998 | Smith et al. | |
| 5,782,928 A | 7/1998 | Ries et al. | |
| 5,874,123 A | 2/1999 | Park | |
| 5,879,405 A | 3/1999 | Ries et al. | |
| 5,928,288 A | 7/1999 | Wilson | |
| 5,931,870 A | 8/1999 | Cuckler et al. | |
| 6,059,833 A | 5/2000 | Doets | |
| 6,136,037 A | 10/2000 | Hassig et al. | |
| 6,162,227 A | 12/2000 | Eckhardt et al. | |
| 6,270,502 B1 | 8/2001 | Stulberg | |
| 6,325,829 B1 | 12/2001 | Schmotzer | |
| 6,344,060 B1 | 2/2002 | Schmotzer et al. | |
| 6,383,228 B1 | 5/2002 | Schmotzer | |
| 6,436,147 B1 | 8/2002 | Zweymuller | |
| 6,451,058 B2 | 9/2002 | Fuke et al. | |
| 6,458,161 B1 | 10/2002 | Gibbs et al. | |
| RE38,058 E | 4/2003 | Fallin | |
| 6,540,788 B1 | 4/2003 | Zweymuller | |
| 6,613,094 B2 | 9/2003 | Zweymuller | |
| 6,626,913 B1 | 9/2003 | McKinnon et al. | |
| 6,652,589 B2 | 11/2003 | Schmotzer et al. | |
| 6,666,870 B2 | 12/2003 | Dixon et al. | |
| 6,746,452 B2 | 6/2004 | Tuke et al. | |
| 6,808,539 B2 | 10/2004 | Zweymuller | |
| 6,916,342 B2 | 7/2005 | Frederick et al. | |
| 6,986,792 B2 | 1/2006 | McLean et al. | |
| 7,004,973 B2 | 2/2006 | Zweymuller | |
| 7,074,241 B2 | 7/2006 | McKinnon | |
| 7,160,307 B2 | 1/2007 | Harwood et al. | |
| 7,160,332 B2 | 1/2007 | Frederick et al. | |
| 7,175,668 B2 | 2/2007 | Zweymuller | |
| 7,179,297 B2 | 2/2007 | McLean | |
| 7,250,054 B2 | 7/2007 | Allen et al. | |
| 7,255,701 B2 | 8/2007 | Allen et al. | |
| 7,335,231 B2 | 2/2008 | McLean | |
| 7,374,576 B1 | 5/2008 | Ries et al. | |
| 7,455,693 B2 | 11/2008 | Zweymuller | |
| 7,494,510 B2 | 2/2009 | Zweymuller | |
| 7,497,875 B1 | 3/2009 | Zweymuller | |
| 7,534,271 B2 | 5/2009 | Ries et al. | |
| 7,575,603 B2 | 8/2009 | Bergin et al. | |
| 7,591,821 B2 | 9/2009 | Kelman | |
| 7,621,915 B2 | 11/2009 | Frederick et al. | |
| 7,682,393 B2 * | 3/2010 | Trieu | A61B 17/1631 623/17.11 |
| 7,682,398 B2 | 3/2010 | Croxton et al. | |
| 7,749,277 B2 | 7/2010 | McLean | |
| 7,749,278 B2 | 7/2010 | Frederick et al. | |
| 7,766,948 B1 | 8/2010 | Leung | |
| 7,780,667 B2 | 8/2010 | Watanabe et al. | |
| 7,794,502 B2 | 9/2010 | Michelson | |
| 7,806,911 B2 | 10/2010 | Peckham | |
| 7,828,806 B2 | 11/2010 | Graf et al. | |
| 7,863,410 B2 | 1/2011 | Smith et al. | |
| 7,879,106 B2 | 2/2011 | McMinn | |
| 7,892,290 B2 | 2/2011 | Bergin et al. | |
| 7,901,411 B2 | 3/2011 | Frederick et al. | |
| 7,985,260 B2 | 7/2011 | Keefer et al. | |
| 7,993,408 B2 | 8/2011 | Meridew et al. | |
| 8,105,367 B2 | 1/2012 | Austin et al. | |
| 8,123,814 B2 | 2/2012 | Meridew et al. | |
| 8,343,196 B2 | 1/2013 | Schneider | |
| 8,382,807 B2 | 2/2013 | Austin et al. | |
| 8,506,607 B2 * | 8/2013 | Eckhof | A61B 17/8057 606/286 |
| 8,506,643 B2 | 8/2013 | Keefer et al. | |
| 8,551,181 B2 | 10/2013 | Meridew et al. | |
| 8,574,268 B2 * | 11/2013 | Chan | B23G 1/02 606/280 |
| 8,597,365 B2 | 12/2013 | Meridew | |
| 8,608,744 B2 | 12/2013 | Ries et al. | |
| 8,728,129 B2 | 5/2014 | Fritzinger et al. | |
| 8,758,346 B2 | 6/2014 | Koay et al. | |
| 8,828,089 B1 | 9/2014 | Perez et al. | |
| 8,834,535 B2 | 9/2014 | McClintock | |

(56) References Cited

U.S. PATENT DOCUMENTS

| | | | |
|---|---|---|---|
| 8,834,536 | B2 | 9/2014 | Elsbury |
| 9,241,801 | B1* | 1/2016 | Parry .................. A61F 2/30749 |
| 9,248,023 | B2 | 2/2016 | Ries et al. |
| 2003/0065397 | A1 | 4/2003 | Hanssen et al. |
| 2003/0125809 | A1 | 7/2003 | Tannotti et al. |
| 2005/0021148 | A1 | 1/2005 | Gibbs |
| 2006/0074430 | A1 | 4/2006 | Deffenbaugh et al. |
| 2006/0264946 | A1 | 11/2006 | Young |
| 2007/0088443 | A1 | 4/2007 | Hanssen et al. |
| 2007/0093836 | A1 | 4/2007 | Derouet |
| 2007/0250175 | A1 | 10/2007 | Meridew et al. |
| 2008/0021568 | A1* | 1/2008 | Tulkis ................. A61F 2/30734 623/22.35 |
| 2009/0143824 | A1 | 6/2009 | Austin et al. |
| 2009/0204225 | A1* | 8/2009 | Meridew .................... A61F 2/34 623/22.21 |
| 2009/0326670 | A1* | 12/2009 | Keefer ....................... A61F 2/34 623/22.22 |
| 2010/0161064 | A1 | 6/2010 | Kellar et al. |
| 2012/0016485 | A1 | 1/2012 | Sharp |
| 2012/0109137 | A1 | 5/2012 | Iannotti et al. |
| 2012/0143193 | A1 | 6/2012 | Hulliger |
| 2013/0338786 | A1* | 12/2013 | Haidukewych ... A61M 5/31596 623/22.32 |
| 2014/0276870 | A1 | 9/2014 | Eash |

FOREIGN PATENT DOCUMENTS

| | | |
|---|---|---|
| CN | 2684790 Y | 3/2005 |
| CN | 101172061 A | 5/2008 |
| CN | 201668539 U | 12/2010 |
| CN | 102048600 A | 5/2011 |
| CN | 102300520 A | 12/2011 |
| DE | 202011050057 U1 | 7/2011 |
| EP | 2140835 A1 | 1/2010 |
| FR | 2519248 A1 | 7/1983 |
| FR | 2633509 A1 | 1/1990 |
| JP | 2008532716 A | 8/2008 |
| JP | 2009502336 A | 1/2009 |
| JP | 2010012254 A | 1/2010 |
| JP | 2011511699 A | 4/2011 |
| WO | 200020083035 A2 | 10/2002 |
| WO | 2006099751 A1 | 9/2006 |
| WO | 2007014192 A2 | 2/2007 |
| WO | 2011012892 A1 | 2/2011 |

OTHER PUBLICATIONS

Second Office Action for Chinese Patent Application No. 201710685364. 1, dated Jul. 29, 2019.

Australia Examination report No. 2 for standard patent applicaiton No. 2019213389, dated Dec. 23, 2020, 4 pages.

Chinese Search Report; State Intellectual Property Office, Peoples Republic of China; Chinese Patent Application No. 201710685364. 1; dated Sep. 18, 2018; 6 pages.

Chinese Office Action (1st); State Intellectual Property Office, Peoples Republic of China; Chinese Patent Application No. 201710685364.1; dated Sep. 29, 2018; 13 pages.

Canadian Office Action; Canadian Intellectual Property Office; Canadian Patent Application No. 2,858,553; dated Jul. 27, 2018; 4 pages.

Australian Examination Report; Australian Patent Office; Australian Patent Application No. 2017213493; dated Aug. 9, 2018; 4 pages.

Australian Examination Report, Australian Patent Office, Australian Patent Application No. 2017279646, dated May 16, 2018, 4 pages.

Japanese Notice of Reasons for Rejection; Japanese Patent Office; Japanese Patent Application No. 2017-194155; dated Jul. 9, 2018; 4 pages.

Australian Examination Report; Australian Patent Office; Australian Patent Application No. 2012347730; dated Aug. 12, 2016; 3 pages.

Japanese Decision of Rejection; Japanese Patent Office: Japanese Patent Application No. 2014546071, dated Jul. 21, 2017, 5 pages.

Australian Examination Report No. 1; Australian Patent Office; Australian Patent Application No. 2012347700; dated Oct. 14, 2016; 4 pages.

Chinese Office Action; Chinese Patent Office; Chinese Patent Application No. 201280069283.4; dated Apr. 15, 2016; 17 pages.

Chinese Office Action; Chinese Patent Office; Chinese Patent Application No. 201280069276.4; dated May 13, 2016; 12 pages.

Chinese Search Report; Chinese Patent Office; Chinese Patent Application No. 201280069276.4; dated May 4, 2016; 4 pages.

Chinese Office Action; Chinese Patent Office; Chinese Patent Application No. 201280069283.4; dated Dec. 1, 2016; 13 pages.

Chinese Office Action; Chinese Patent Office; Chinese Patent Application No. 201280069276.4; dated Feb. 13, 2017; 14 pages.

European Search Report; European Patent Office; European Patent Application No. 12854571.2; dated Jun. 25, 2015; 7 pages.

Australian Examination Report (2nd), Australian Patent Office, Australian Patent Application No. 2017279646, dated Jun. 18, 2018, 2 pages.

Australian Examination Report No. 2; Australian Patent Office; Australian Patent Application No. 2012347730; dated Aug. 7, 2017; 4 pages.

Canadian Office Action; Canadian Intellectual Property Office; Canadian Patent Application No. 2,858,559; dated Aug. 31, 2018; 3 pages.

Chinese Office Action; Chinese Patent Office; Chinese Patent Application No. 201280069276.4; dated Oct. 24, 2017; 9 pages.

European Examination Report; European Patent Office; European Patent Application No. 12855969.7; dated Jun. 28, 2016 4 pages.

European Examination Report; European Patent Office; European Patent Application No. 12854571.2; dated Nov. 29, 2016; 4 pages.

PCT International Search Report dated Mar. 25, 2013, International Application No. PCT/US2012/068304; 14 pages.

Japanese Notice of Reasons for Rejection; Japanese Patent Office; Japanese Patent Application No. 2014-546071; dated Sep. 26, 2016; 10 pages.

International Search Report dated Mar. 13, 2013; International Application No. PCT/US2012/068219; 12 pages.

Japanese Notice of Reasons for Rejection; Japanese Patent Office; Japanese Patent Application No. 2014-546096; dated Oct. 3, 2016; 11 pages.

Australian Examination Report No. 2; Australian Patent Office; Australian Patent Application No. 2012347700; dated Jul. 20, 2017; 3 pages.

PCT International Search Report dated Mar. 28, 2013, International Application No. PCT/US2012/068222; 14 pages.

European Office Action; European Patent Office; European Patent Application No. 12854571.2; dated Jul. 24, 2018; 4 pages.

Australian Examination Report No. 2 for Australian Patent Application No. 2017213493, dated Jun. 27, 2019.

Australian Examination Report No. 3 for Australian Patent Application No. 2017213493, dated Aug. 1, 2019.

Examination report No. 1 for Australian Patent Application No. 2019213389, dated Jul. 2, 2020.

Third Office Action for Chinese Patent Application No. 201710685364. 1, dated Apr. 22, 2020.

Examination Report for Indian Patent Application No. 4606/DELNP/2014, dated Feb. 28, 2020.

Examination Report for Indian Patent Application No. 4617/DELNP/2014, dated Mar. 18, 2020.

First Office Action for Chinese Patent Application No. 2018111291140, dated Dec. 30, 2019.

* cited by examiner

ORTHOPEDIC IMPLANT AUGMENTS

CROSS-REFERENCE TO RELATED APPLICATION

This application is a continuation of pending U.S. patent application Ser. No. 15/653,055, filed Jul. 18, 2017, which a continuation of U.S. patent application Ser. No. 14/363,775 filed Jun. 6, 2014 and issued U.S. Pat. No. 9,707,097, which is a United States National Phase of International PCT Application No. PCT/US2012/068219 filed Dec. 6, 2012, which claims the benefit of U.S. Provisional Patent Application Ser. No. 61/567,971 filed Dec. 7, 2011, the contents of each application hereby incorporated by reference in their entirety.

BACKGROUND

Joints often undergo degenerative changes due to a variety of reasons. When degeneration becomes advanced or irreversible it may become necessary to replace a motive joint with a prosthetic joint. Degenerative disease or injury may require replacement of all or a portion, of a patient's joint using synthetic material, typically metals, ceramics, or polymer materials. Artificial implants, including hip implants, shoulder implants and knee implants made from these materials, are widely used in orthopedic surgery to strengthen or replace degenerating joints.

In a primary replacement surgery, a patient's native joint is replaced with a prosthetic implant. The implant is designed to integrate with the patient's bone and provide the same function and motion as the native joint that is being replaced. After a primary replacement, it may become necessary to conduct a second or subsequent revision surgery in order to replace a prosthetic joint with a replacement joint which is often larger than the primary replacement. Such surgeries often become necessary due to further degeneration of bone or advancement of a degenerative disease requiring replacement of the implant and diseased bone with a larger, enhanced prosthetic joint, often referred to as a revision prosthesis. For example, bone is often lost around the rim of an acetabulum around a hip implant, and thus may provide less rim coverage to securely hold a press-fit acetabular shell. A larger shell can be placed into the acetabulum in a revision surgery to make up for the lost bone.

In both primary and revision replacement surgeries, a patient's native bone may have defects or voids that a surgeon can fill with bone grafts before inserting an implant. This process may be time consuming and expensive and may subject the patient to health risks. In order to facilitate successful implants in a bone having defects or voids, a surgeon may use implant augments in conjunction with standard implant components to fill in the voids. Such augments can be coupled or otherwise attached to an outer surface of an implant in the area of a bone void or defect in the native bone. In addition to primary surgery, augments are often used in revision surgeries due to bone degeneration, bone loss or other defects in the degenerative area that necessitates the revision surgery.

A degree of variability in implant augments may be desired, as the location and nature of the native bone and the bone defects vary from patient to patient. Especially when defects or voids in the bone are present, it is preferable for a surgeon to have the ability to adjust the implant to fit the bone, rather than adjusting the bone to fit a rigid implant. Adjusting the implant or implant augments allows for conservation of native bone rather than requiring reaming or other removal of a patient's native bone in preparation for implant placement. Conserving bone supplements the support that the bone gives to the implant component. Especially in the cases of diseased bone or damaged bone in revision surgery, any bone that is removed to prepare for the implant may prove detrimental to the integrity of the bone and its ability to withstand significant forces following implantation.

To supplement fixation of orthopedic implants into native bone, implants can incorporate mechanical fasteners, such as screws, and locking mechanisms that engage the screws in a locked configuration relative to both the bone and the implant. Such fasteners and locking mechanisms can be used to hold the implant in place and reduce detrimental effects caused by implant movement. While the locking mechanism provide a steady hold between the fastener and the implant, the nature of the locking mechanisms often limits the orientation in which the fastener can be locked. The locking mechanisms often require that the fastener be inserted in a certain direction along a given axis in order to engage the locking mechanism of the implant.

Implementing locking screws and locking mechanism into implant augments may be desirable to increase the hold of the implants and augments into native bone. The locking mechanisms may also, however, cut down on variability of augments the number of orientations in which an augment can be inserted into a bone, given the limited function of the locking mechanisms. Incorporating a locking mechanism into an augment may require a surgeon to choose between placing, the augment in an orientation with a strong hold of the locking mechanisms or placing the augment in an orientation that creates better contact with the native bone into which the augment is placed, but creates a weaker engagement of the locking mechanism. This can create problems and result in inadequate fixation of an augment or an undesirable positioning of the augment in native bone.

SUMMARY

Disclosed herein are systems, devices and methods for providing implant augments that allow for intraoperative variability and supplemented fixation into native bone. In general, the systems, devices and methods provide augments that include one or more locking mechanisms that engage mechanical fasteners and fix the augments into bone. The locking mechanisms are configured such that the augment may be inserted in a wide variety of orientations, allowing the locking mechanism to engage a mechanical fastener in each of the possible orientations. These augments provide a combination of adequate bone fixation and locking engagement with mechanical fasteners while still maintaining close contact with both the patient's native bone and an implant placed into that bone.

In some embodiments, an orthopedic device, such as an augment, includes a first surface having a mating face that is configured to mate with an implant and an opening configured to receive a fastener. The opening includes a plurality of fins that are disposed in a plane that is not parallel to the mating face of the first surface.

In certain implementations, the opening in the device includes first and second ends, and the opening is configured to receive a fastener inserted into the first end when the device is in a first orientation and is configured to receive a fastener inserted into the second end when the device is in a second orientation. The fins are disposed between the first and second end or the opening and are configured to lock a fastener in a first locked configuration when the device is in the first orientation and are configured to lock a fastener in a second locked configuration when the device is in the second orientation.

The mating face is configured to mate with an implant when the device is in each of the first and second orientations. The orthopedic device also includes a second surface configured to mate with the patient's bone or tissue, and the second surface configured to mate with patient's bone or tissue when the device is in each of the first and second orientations.

In certain implementations, the plane in which the fins are disposed is substantially perpendicular to the mating face. The fins are configured to engage a fastener inserted along any one of a plurality of axes and lock the fastener in a plurality of locking configurations corresponding to the plurality of axes.

In some embodiments, an orthopedic device includes a means for mating with an implant, a means for receiving a fastener and a means for locking a fastener disposed in a plane that is not parallel to the means for mating with an implant.

BRIEF DESCRIPTION OF THE DRAWINGS

The foregoing and other objects and advantages will be more appreciated fully from the following further description thereof with reference to the accompanying drawings. These depicted embodiments are to be understood as illustrative, and not a limiting in any way.

DETAILED DESCRIPTION

To provide an overall understanding of the systems, devices and methods described herein, certain illustrative embodiments will now be described. In general, the systems, devices and methods provide augments that include one or more locking mechanisms that engage mechanical fasteners and fix the augments into bone. For the purpose of clarity and illustration the systems, devices and methods are described with respect to orthopedic implant augments but it will be understood by one of ordinary skill in the art that the systems, devices and methods disclosed herein may be adapted and modified as appropriate, and that the systems, devices and methods described herein may be employed in other suitable applications such as where other types of implants or augments, or may utilize other types of locking mechanisms, and that such other additions and modifications will not depart from the scope hereof.

The augments described herein provide a surgeon with adjustability and variability to accommodate a wide variety of bone anatomies. The augments preferably maintain a close interface with both an implant and a patients surrounding bone while allowing the surgeon to place the augments in a wide variety of positions in order to suit different bone anatomies. In addition, the augments incorporate locking mechanisms that lock mechanical fasteners into the augment in a locking configuration. These locking mechanisms are disposed and aligned such that the movement of the augment from one orientation to a variety of either orientations does not materially interfere with the locking mechanism and also does not materially interfere with the close interfaces with the implant and surrounding bone.

Figure 1A:
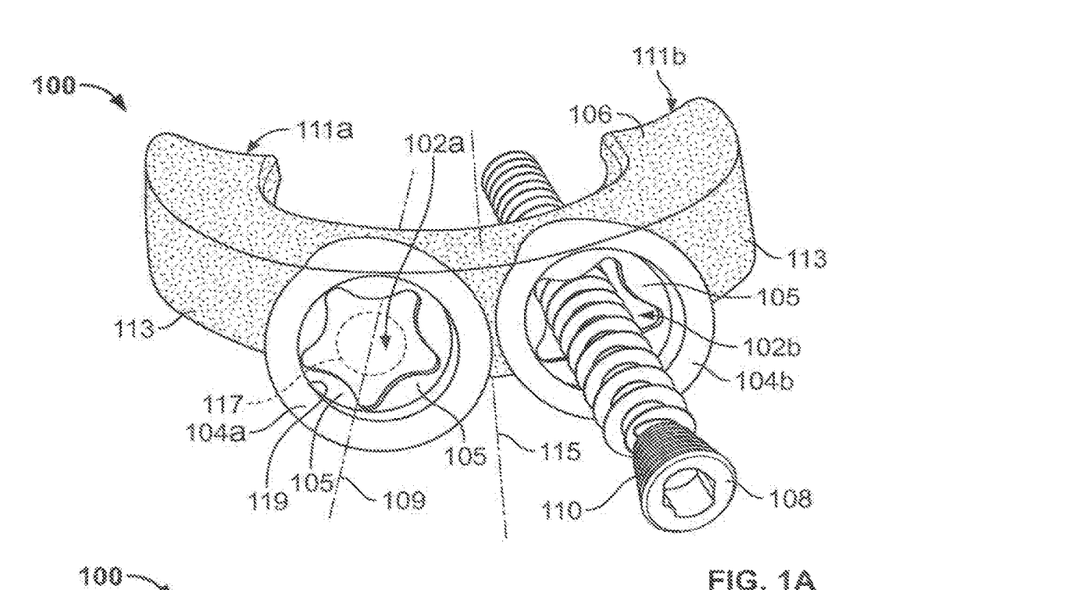
FIGS. 1A and 1B show perspective views of an illustrative augment having a fastener locking mechanism.
Figure 1B:
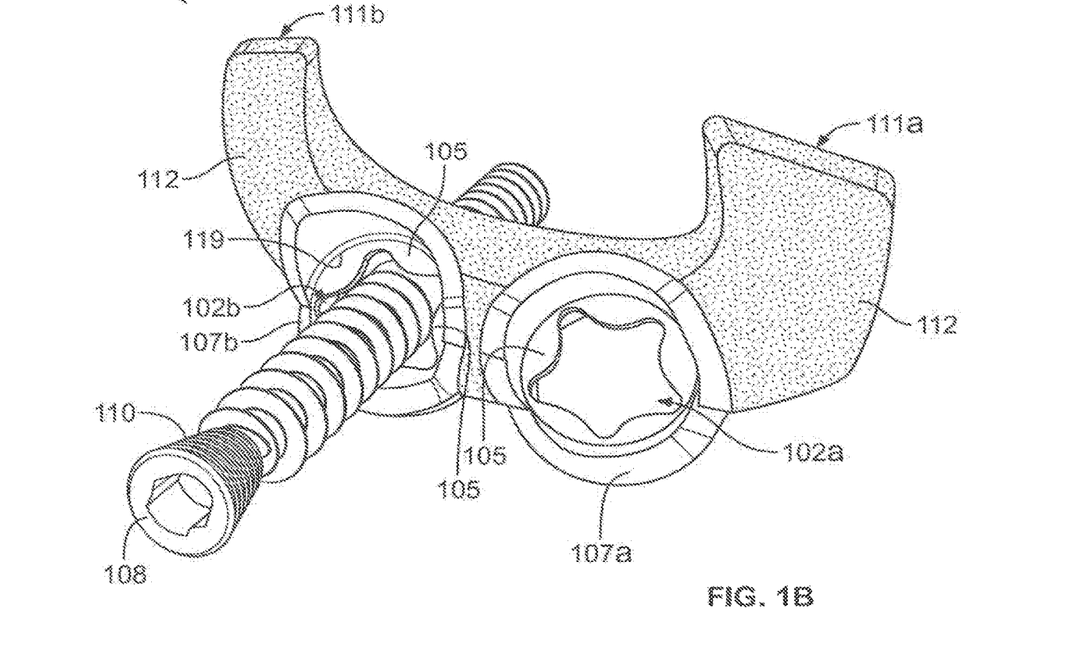

FIGS. 1A and 1B show perspective views of an implant augment 100. The augment 100 has a generally horseshoe shape with two legs 111a and 111b extending below a top surface 113. The augment includes two openings 102a and 102b that extend from the top surface 113. The two openings 102a and 102b are configured to receive a mechanical fastener, such as screw 108, to fix the augment 100 to bone into which the augment is implanted.

The inner surface of the augment 100 has a mating face 106. The mating face 106 is designed to match the shape of an exterior surface of an implant, such as an acetabular shell or cage. The mating face 106 extends down both of the legs 111a and 111b and has an arcuate contour and smooth face to maintain a close contact with a given implant when the augment 100 is positioned in a variety of orientations and rotations.

Each of the openings 102a and 102b has a first end 104a and 104b, respectively, that extends above the top surface 113 of the augment. Each opening 102a and 102b includes a plurality of fins 105 disposed therein that create a locking mechanism within the openings. The openings 102a and 102b are shown in FIGS. 1A and 1B with five fins 105 extending inward from interior surfaces of the openings 102a and 102b, but any other suitable number of fins may be used. A longitudinal axis, for example, axis 109 shown in FIG. 1A, runs through each of the openings 102a and 102b. The longitudinal axis 109 is substantially parallel to the flat surface of the mating face 106. In this orientation, the fins 105 and both openings 102a and 102b are disposed in a plane that is normal to the axis 109. Thus, the plane in which the fins 105 are disposed is also substantially perpendicular to the smooth mating face 106.

The fins 105 are configured to engage a mechanical fastener, such as the screw 108, to lock the fastener into the augment 100 when the fastener is inserted into either of the openings 102a or 102b. The fins 105 extend inward from the interior surface 119 of the opening 102a toward the longitudinal axis that runs through the center of the opening. When the screw 108 is inserted into the opening, the fins 105 engage the threading 110 on the head of the screw 108. The engagement between the fins 105 and the threading 110 locks the screw 108 into either of the openings 102a and 102b. The interaction between the fins 105 and the threading 110 resists removal of the screw 108.

In addition to locking a fastener in place the openings 102a and 102b allow for polyaxial alignment of fasteners inserted into one of the openings. The width of the openings and space between the fins 105 allows for movement of the screw 108 to align along an axis through the opening that is offset from the axis 109. The dotted outline 117 shown within opening 102a indicates the width of the screw 108, and shows the extra spacing between the fins 105 that allows the screw to move freely. With this extra space, a screw can be twisted to align with a variety of axes offset from the axis 109. Because the fins 105 are disposed around the inner perimeter of the opening 102a, the locking engagement between the fins 105 and the threading 110 is maintained at any of the varieties of axes along which the screw 108 may be inserted. Thus, the openings 102a and 102b and the locking fins 105 not only allow for the augment 100 to lock onto a fastener and connect the augment to the bone, but also may accommodate fasteners inserted at any of a variety of angles along any variety of axes in order to further enhance the variability and adjustability of the augment 100.

The orientation of the openings 102a and 102b relative to the mating face 106 allows for the augment 100 to be implanted in a variety of orientations while still maintaining adequate locking engagement between the screw 108 and one of the openings. When the augment is implanted in a certain chosen orientation, the alignment of the openings 102a and 102b also allows close contact to be maintained between the mating face 106 and an implant, as well as allowing for close contact to be maintained between an exterior surface or the augment 100 and the patient's native bone. For example, the augment 100 shown in FIG. 1A may be rotated about the axis 115, which runs perpendicular to the mating face 106. Such rotation produces a variety of orientations in which the augment can be placed with the mating face 106 facing substantially the same direction while the openings 102a and 102b are rotated. When the augment 100 is rotated around axis 115, maintaining the position of the mating face 106 in a single direction will allow the mating face 106 to continue to contact an implant next to which the augment 100 is placed.

To further facilitate the variability of the augment 100 while maintaining the orientation of the mating face 106, the openings 102a and 102b are able to receive and lock a fastener inserted into either end of the openings. FIG. 1B shows a second perspective view of the augment 100 with second ends 107a and 107b of the openings 102a and 102b, respectively, exposed. As shown in FIG. 1B, a fastener, such as the screw 108, can also be inserted through the second ends 107a and 107b of the openings. The openings 102a and 102b and the fins 105 are designed such that the locking engagement between the fins 105 and threads 110 of the screw 108 is not unidirectional, and the locking interaction can occur regardless of the direction in which the screw 108 is inserted into one of the openings. As shown in FIG. 1B, the screw 108 passes through the opening 102b such that the threads 110 are able to engage the fins 105, similar to the orientation shown in FIG. 1A, in which the screw 108 is inserted into the first end 104 of the opening 102b.

The orientation of the openings 102a and 102b and the locking fins 105 relative to the mating face 106 allows for the augment 100 to maintain a close interface with an implant when the screw 108 is inserted to the second ends 107a and 107b of the opening. Because the fins 105 are not parallel to the mating face 106, the rotation around the axis 105 shown in FIG. 1A, and insertion of the screw 108 into the second end 107b of opening 102b, can be achieved without affecting the positioning of the mating face 106. Likewise, the bone interface surface 112 is maintained in a position to contact the patient's native bone when the augment 100 is rotated around axis 115. Like the mating faces 106, the bone interface surface 112 maintains close contact with the bone when the screw 108 is inserted through either the first ends 104a and 104b or second ends 107a and 107b of the openings. This alignment of the openings 102a and 102b allows a wide range of variability in the orientations in which a surgeon can insert the augment 100 while still maintaining the desired contact between the mating face 106 and an implant and the bone interface surface 112 and the patient's bone, and also maintaining the ability to lock the screw 108 into the opening. The polyaxial nature of the openings 102a and 102b and the locking fins 105 further supplements the wide variability of the augment 100.

Figure 2:
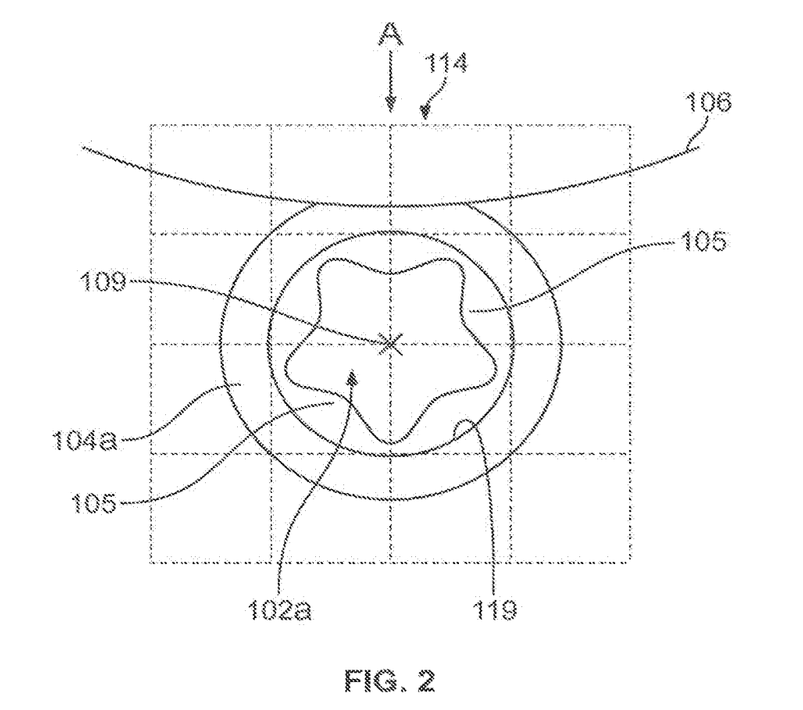
FIG. 2 depicts one of the locking mechanisms of the augment shown in FIGS. 1A and 1B.

The orientation of the fins 105 relative to the mating face 106 and the bone interface surface 112 provides variability in placing the augment while maintaining the desired positioning of the mating face 106 with an implant and the bone interface surface 112 with a patient's bone. FIG. 2 further illustrates the orientation of the fins 105 in a top view of the opening 102a of the augment 100. As shown in FIG. 2, the fins 105 are disposed on the interior of the opening 102a, extending inwardly from the interior surface 119 of the opening toward the center longitudinal axis 109 of the opening. The fins 105 extend substantially perpendicular to the interior surface 119, and thus each of the fins 105 is substantially disposed within a plane 114 shown in FIG. 2. The plane 114 is normal to the longitudinal axis 109 of the opening 102a and shows the alignment of the fins 105 relative to the mating face 106. As shown in FIG. 2, the plane 114 intersects the mating face 106 and is not parallel to the mating face 106. In the embodiment shown in FIG. 2, the plane 114 is perpendicular to the mating face 106, but in other embodiments, the plane may be skewed slightly so as not to be completely perpendicular to the mating face.

In general, the orientation of the fins 105 relative to the mating face 106 allows the opening 102a to receive a fastener at a variety of angles, positions and directions. In particular, because the fins 105 are disposed in the plane 114 substantially perpendicular to the mating face 106, a screw may be received by the opening 102a either through the first end 104a of the opening, shown in FIG. 2, or through the second end 107a of the opening, not shown in FIG. 2, that is from the back or the front of the opening. This allows the surgeon to more flexibly select the location and direction of screw insertion. It also allows the mating face 106 to remain in close contact with an implant regardless of the end of the opening 102a into which the screw is inserted. This close contact would not be possible if for example, the opening 102a and fins 105 were aligned parallel with the mating face 106, as opposed to the perpendicular alignment shown in FIG. 2. If the opening and fins were parallel to the mating face, the screw would break the plane of the mating face. This would present a close contact between the mating face and an implant, as a screw could not be inserted in the direction shown by arrow A in FIG. 2 with the mating face 106 placed in close contact with an implant. This complication is avoided by the orientation of the fins 105 and opening 102a, as the screw can be inserted from either end of the opening, when the mating face 106 is maintained in close contact with an implant.

The variability afforded by the augment 100 provides a surgeon with the ability to adjust the augment to fit specific needs or bone anatomy of a particular surgery. This variability allows the surgeon to make decisions intraoperatively and determine the orientation that best fills the need for the surrounding bone anatomy. For example, the surgeon may view the surgical field with an implant placed in the patient's bone and determine the optimal orientation of the augment to fill a defect or void in the patient's bone. The surgeon is then able to position the augment in the desired orientation and insert a screw into whichever end of the opening to the augment will better engage the patient's bone and lock the screw in a locked configuration. Alternatively, the variability of the augment gives a surgeon the ability to decide pre-operatively the orientation of the augment that best fits the needs of the patient's bone. In some approaches, this may require multiple different augments that allow the surgeon to achieve one of the selected orientations. However, the variability of the augment 100 allows the surgeon to use just the single augment to achieve whichever orientation he or she desires. Whether the decision is made pre-operatively or intra-operatively, the surgeon is able to position the augment in the orientation that best fits the needs of the native bone while maintaining a close contact between a mating face of the augment and the implant, as well as a close contact between a bone interface surface of the augment and the patient's surrounding bone. All of these interactions are maintained while at the same time allowing a screw to be inserted and locked into the augment in whichever orientation is selected. The polyaxial nature of the openings and locking mechanisms of the augment further contribute to the ability of the surgeon to locate the augment and screws as desired.

Figure 3A:
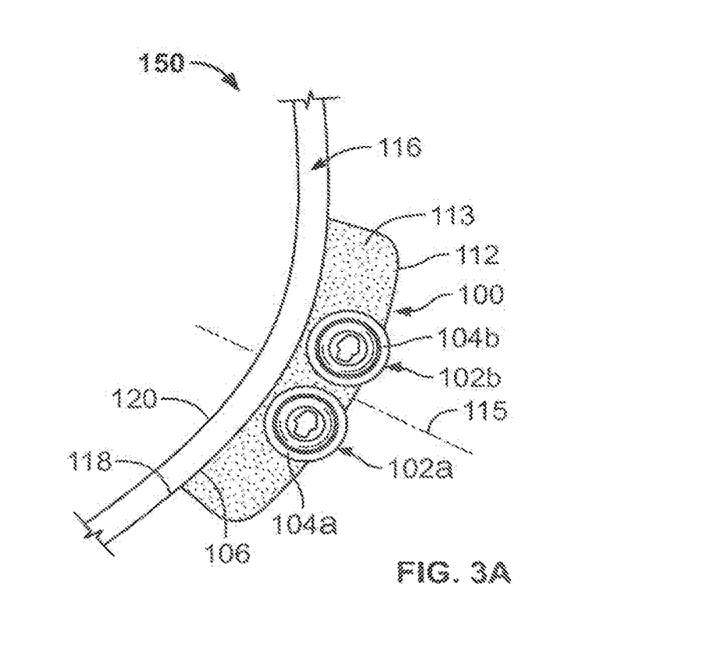
FIGS. 3A-3C show various illustrative orientations in which the augment of FIGS. 1A and 1B may be attached to an implant.
Figure 3B:
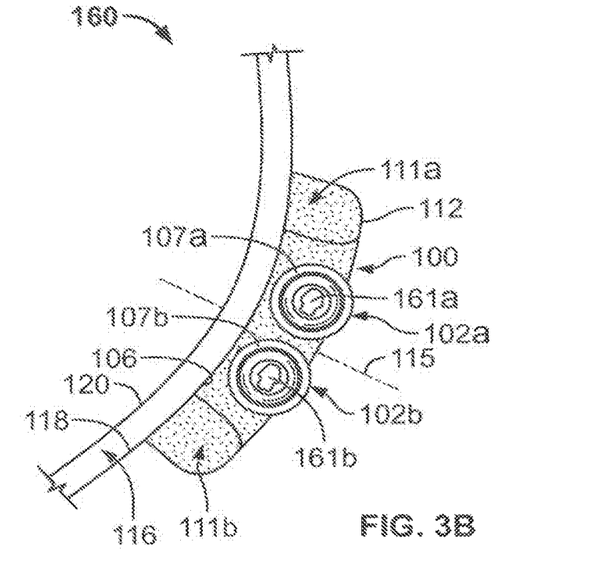
Figure 3C:
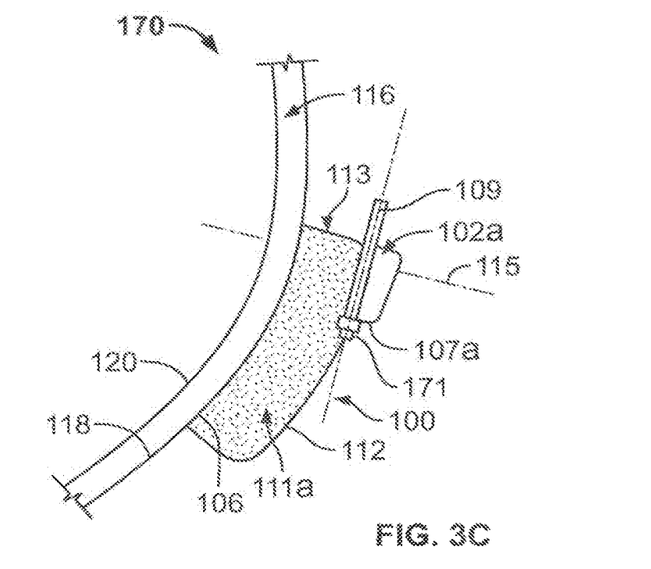

FIGS. 3A-3C show three configurations that highlight variability of the augment 100. FIG. 3A shows a first configuration 150 in which the augment 100 is implanted with an acetabular shell. The augment 100 is shown in FIG. 3A abutting a rim 116 of the implanted shell, with the rim 116 having an exterior surface 118 and an interior surface 120. In the configuration shown in FIG. 3A, the augment 100 is placed against an exterior surface of the rim 116. In this orientation, the two legs 111a and 111b, not shown in FIG. 3A, extend downward away from the top surface 113. This orientation may be desired, for example, if there is a screw implanted with the shell and holding the shell into a patient's bone. By inserting the augment 100 in the orientation shown in FIG. 3A, the two legs 111a and 111b are able to pass on either side of the screw and allow the augment 100 to be implanted without interfering with the screw.

Rather than the augment orientation shown in FIG. 3A, a surgeon may desire to place the augment 100 in alternate configurations. The variability of the augment 100 allows the surgeon to rotate the augment 100 about the axis 115, shown in FIG. 3A in order to achieve other augment orientations while maintaining the contact between the mating face 106 of the augment and the exterior surface 118 of the implant. FIG. 3B shows one alternate orientation in which the augment 100 is rotated 180 degrees about axis 115 from the orientation shown in FIG. 3A. In the orientation 160, shown in FIG. 3B, the augment is placed such that the top surface 113 of the augment is positioned down into the bone, and the two legs 111a and 111b are facing up toward the top rim 116 of the implant. In this orientation, the close contact is maintained between the mating surface 106 of the augment and the exterior surface 118 of the implant. Additionally, the location of the bone interfacing surface 112 is maintained facing away from the native implant such that it is able to contact a patient's native bone. The orientation 160 may be desired if, for example, the surgeon determines that there is a bone void or a need for more support in lower portions of the implanted shell. By positioning the augment 100 in the orientation 160, the surgeon can position the top portion of the augment 100, which has more material and more support, down toward the bottom of the native implant, where that support is needed.

To facilitate the placement of the augment 100 in the orientation 160, the screws 161a and 161b are inserted into the second ends 107a and 107b of the openings 102a and 102b. The polyaxial and multidirectional nature of these openings allows for the screws to be locked into the openings in this alternate orientation. Because the openings and the locking mechanisms work in multiple directions, the orientation 160 may be achieved while keeping the desired contact with both the patient's bone and the native implant, and still taking advantage of the available locking mechanism of the augment 100.

In addition to the two orientations shown in FIGS. 3A and 3B, any intermediate rotation that may be desired can be achieved with the augment 100. FIG. 3C shows a third orientation 170 of the augment 100 placed against the native implant. As shown in FIG. 3C, the augment 100 is rotated 90 degrees about the axis 115 from the orientation shown in FIG. 3B. This rotation positions the implant such that leg 111a dices toward the top of the implant rim 116. In the orientation 170, the close contact between the mating face 106 of the augment and the exterior surface 118 of the rim 116 is again maintained. Also, the positioning of the bone interface surface 112 is maintained facing away from the rim 116 so that it may contact the patient's native bone. The screw 171 is inserted into the second end 107a of the opening 102a and extends through the opening beyond the top surface 113 of the augment. Because the center axis 109 of the opening 102a does not extend away from the patient's native bone as it does in FIGS. 3A and 3B, placement of the screw may be more difficult than screw placement in the orientation 150 and 160. The polyaxial nature of the opening 102a and the locking fins that maintain the screw in the opening 102a can facilitate the placement of the screw off-axis from the center axis 109 to still allow the surgeon to secure the screw into the patient's bone and lock the screw in its orientation with the augment 100.

Figure 4:
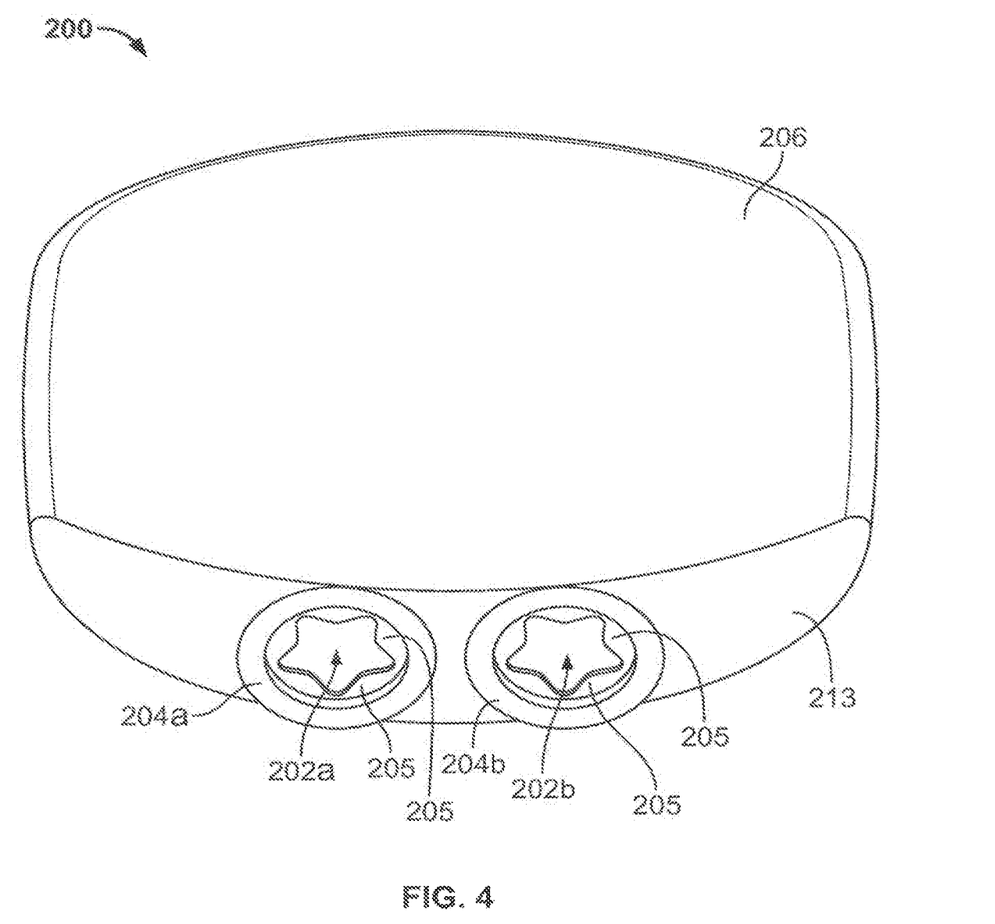
FIG. 4 shows a perspective view of an illustrative augment having a fastener locking mechanism.

While the augment 100 is shown having a horseshoe shape to highlight certain advantages and applications of the augment, alternative embodiments of the augment may take any form or shape that is suitable for a particular application. FIG. 4 shows an augment 200 which has an alternate shape. The augment has a full mating face 206 that does not have a gap, as the mating face 106 of augment 100 has between the legs 111a and 111b. This shape augment may be desirable for applications in which there is a large bone void to fill, or when there are no screws in a native implant to be avoided. The augment 200 includes a top surface 213 into which two openings 202a and 202b pass. Each of the openings 202a and 202b include locking fins 205 disposed from an interior surface of the opening. Similar to the openings and locking fins discussed above with respect to augment 100, the openings 202a and 202b can receive a fastener through either of the first ends 204a or 204b of the opening or second ends, which are not shown in FIG. 4. The fins 205 are disposed in a plane that is not parallel to the mating face 206. Thus, the multidirectional, polyaxial nature of the openings 202a and 202b and the fins 205 allow the augment 200 to be placed in a variety of orientations that maintain close contact between the mating face 206 and an implant, and also allow a surgeon to utilize the locking mechanism of the openings 202a and 202b.

It is to be understood that the foregoing description is merely illustrative, and is not to be limited to the details given herein. While several embodiments have been provided in the present disclosure, it should be understood that the disclosed systems, devices and methods and their components may be embodied in many other specific forms without departing from the scope of the disclosure.

Variations and modifications will occur to those of skill in the art after revealing this disclosure, where disclosed features may be implemented in any combination and subcombinations (including multiple dependent combinations and subcombinations), with one or more other features described herein. The various features described are illustrated above, including an components thereof, may be combined or integrated in other systems, moreover, certain features may be omitted or not implemented.

Examples of changes, substitutions and alterations are ascertainable by one skilled in the art and to be made without departing from the scope of the information disclosed herein. All references cited herein are incorporated by reference in their entirety, and made part of this application.

The invention claimed is:

1. An acetabular system comprising:
   an implant selected from one of an acetabular shell and an acetabular cage, the implant including a rim and an exterior surface; and
   an augment including:
   a body portion and first and second legs extending from opposite ends of the body portion;
   a mating surface adapted and configured to contact the exterior surface of the implant during use, the mating surface having a generally horseshoe shape;
   a first surface intersecting the mating surface along a first edge;
   a second surface intersecting the mating surface along a second edge; and
   a plurality of openings extending from the first surface to the second surface, at least one of the openings including a plurality of fins extending inwardly from an inner surface of the opening, the plurality of fins being adapted and configured to selectively secure a position of a fastener inserted therein along any one of a variety of angles for securing the augment to a patient's bone during use;
   wherein the plurality of fins are arranged and configured in a plane, the plane being non-parallel to the mating surface; and
   wherein the mating surface is arranged and configured to contact the exterior surface of the implant during use in either a first orientation or a second orientation, in the first orientation, the legs extend from the body portion of the augment towards the rim of the implant, in the second orientation, the legs extend from the body portion of the augment away from the rim of the implant.

2. The system of claim 1, wherein the plane of the fins is substantially perpendicular to the mating surface.

3. The system of claim 1, wherein each of the plurality of openings includes a first end associated with the first surface of the augment and a second end associated with the second surface of the augment, the plurality of openings being adapted and configured to selectively receive a fastener inserted into either of the first end or the second end.

4. The system of claim 3, wherein the fastener is inserted into the first end when the augment is positioned in the first orientation relative to the implant, and the fastener is inserted into the second end when the augment is positioned in the second orientation.

5. The system of claim 4, wherein the augment further comprises a bone contacting surface, the bone contacting surface configured to mate with the patient's bone or tissue in each of the first and second orientations.

6. The system of claim 1, wherein the plurality of fins and the opening are adapted and configured to enable longitudinal movement of a fastener within the opening.

7. The system of claim 1, wherein the opening includes a width, the width of the opening and a space between the plurality of fins being adapted and configured to allow for movement of the fastener so that an axis of the fastener is offset from the central axis of the opening.

8. The system of claim 1, wherein the mating surface of the augment includes an arcuate, contoured shape and the exterior surface of the implant includes an outer curved surface.

9. The system of claim 8, wherein the augment further comprises a bone interface surface opposite the mating surface-fac-e, the bone interface surface having a second contoured shape that mates with a patient's bone or tissue, the arcuate, contoured shape being different than the second contoured shape.

10. The system of claim 9, wherein the bone interface surface is arranged and configured to be non-parallel to the plane of the plurality of fins.

11. The system of claim 1, wherein at least a portion of the mating surface is formed from a porous material.

* * * * *